US008345091B2

(12) United States Patent
Amano et al.

(10) Patent No.: US 8,345,091 B2
(45) Date of Patent: Jan. 1, 2013

(54) ENDOSCOPE SYSTEM AND METHOD FOR CONTROLLING ENDOSCOPE ACTUATOR

(75) Inventors: Shoichi Amano, Hachioji (JP); Takayuki Yabuki, Hachioji (JP); Yutaka Fujisawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/343,745

(22) Filed: Jan. 5, 2012

(65) Prior Publication Data

US 2012/0162402 A1 Jun. 28, 2012

Related U.S. Application Data

(63) Continuation of application No. PCT/JP2011/061988, filed on May 25, 2011.

(30) Foreign Application Priority Data

Jul. 8, 2010 (JP) .................................. 2010-156156

(51) Int. Cl.
H04N 9/47 (2006.01)
H04N 7/18 (2006.01)
A62B 1/04 (2006.01)
(52) U.S. Cl. .......................................... 348/65; 606/78
(58) Field of Classification Search .................... 348/65; 606/78
See application file for complete search history.

(56) References Cited

U.S. PATENT DOCUMENTS

| 2008/0278590 A1* | 11/2008 | Tanimura et al. ........ 348/208.99 |
| 2009/0303619 A1 | 12/2009 | Iwasaki et al. |
| 2010/0045214 A1 | 2/2010 | Matsuki |

FOREIGN PATENT DOCUMENTS

| EP | 2 130 482 A1 | 12/2009 |
| JP | 2009-148369 | 7/2009 |
| JP | 2009-291364 | 12/2009 |
| JP | 2010-048120 | 3/2010 |
| WO | WO 2010073902 A1 * | 7/2010 |

* cited by examiner

Primary Examiner — Mehrdad Dastouri
Assistant Examiner — Jeremaiah C Hallenbeck-Huber
(74) Attorney, Agent, or Firm — Scully Scott Murphy & Presser, PC

(57) ABSTRACT

An endoscope system includes: an actuator having an SMA wire and driving a moving member for moving a lens; an output control circuit; a detection circuit; and a CPU. The CPU outputs a driving signal to the output control circuit, on a basis of an instruction to move the lens, and on the basis of a position of the moving member corresponding to a resistance value detected by the detection circuit. In response to a moving instruction to move the lens from a far-point position to a near-point position, the CPU outputs the driving signal so that a current for moving the moving member from the far-point position to a position beyond the near-point position is passed through the SMA wire to heat the SMA wire. The CPU then performs preheating control, holding constant current transition control, and reheating control.

13 Claims, 9 Drawing Sheets

FIG.9

| MAIN CONTROL STATUS | | SUB CONTROL STATUS | STARTING CONDITION | FINISHING CONDITION | CONTROL MODE | DRIVING CURRENT |
|---|---|---|---|---|---|---|
| NEAR-POINT FOCUS SWITCHING INITIAL CONTROL | (A) | INITIAL RESISTANCE CONTROL | INSTRUCTION TO SWITCH TO NEAR POINT | REACH TARGET RESISTANCE VALUE 1 | PD CONTROL | CURRENT COMPUTED WITH PD CONTROL |
| | (B) | PREHEATING CONTROL | REACH TARGET RESISTANCE VALUE 1 | REACH TARGET RESISTANCE VALUE 2 | CONSTANT CURRENT CONTROL | FIRST CONSTANT CURRENT |
| | (C) | HOLDING CONSTANT CURRENT TRANSITION CONTROL | REACH TARGET RESISTANCE VALUE 2 | REACH TARGET RESISTANCE VALUE 3 | CONSTANT CURRENT CONTROL | HOLDING CONSTANT CURRENT (INITIAL VALUE) |
| NEAR-POINT FOCUS HOLDING CONTROL | (D-1) | REHEATING CONTROL (DURING HOLDING) | REACH TARGET RESISTANCE VALUE 3 | REACH TARGET RESISTANCE VALUE 2 | CONSTANT CURRENT CONTROL | SECOND CONSTANT CURRENT |
| | (D-2) | HOLDING CURRENT CHANGING CONTROL | REACH TARGET RESISTANCE VALUE 2 | REACH TARGET RESISTANCE VALUE 3 | CONSTANT CURRENT CONTROL (VARIABLE) | CHANGED BY PREDETERMINED AMOUNT FROM PREVIOUS HOLDING CURRENT |

TBL

ENDOSCOPE SYSTEM AND METHOD FOR CONTROLLING ENDOSCOPE ACTUATOR

CROSS REFERENCE TO RELATED APPLICATION

This application is a continuation application of PCT/JP2011/061988 filed on May 25, 2011 and claims benefit of Japanese Application No. 2010-156156 filed in Japan on Jul. 8, 2010, the entire contents of which are incorporated herein by this reference.

BACKGROUND OF THE INVENTION

1. Field of the Invention

The present invention relates to an endoscope system and a method for controlling an endoscope actuator. Particularly, the present invention relates to an endoscope system having an actuator with a shape memory element for moving an objective optical system, and a method for controlling an endoscope actuator.

2. Description of the Related Art

Endoscope systems have been widely used in medical and industrial fields. An image of an object is picked up with an image pickup device provided in a distal end portion of an endoscope insertion section, and displayed on a monitor apparatus. A person such as a surgeon can perform observation with reference to the object image displayed on the monitor. The image pickup device and an observation optical system are internally provided in the distal end portion of the endoscope insertion section.

In recent years, as disclosed in Japanese Patent Application Laid-Open Publication No. 2009-148369, an endoscope apparatus has been proposed in which a mechanism for a focusing function for an object image is provided in the insertion section to cause a lens frame of the observation optical system to be moved in the optical axis direction. The apparatus uses a shape memory alloy as an actuator for moving the lens frame.

The shape memory alloy wire is elongated and contracted by controlling a current passed through the wire. For example, the shape memory alloy wire produces heat in response to passage of the current and is contracted at high temperatures; whereas it releases heat in response to shutoff of the current and is elongated consequently. Such characteristics of the shape memory alloy are utilized to realize the focusing function of the observation optical system.

In regard to an actuator with a shape memory alloy, Japanese Patent Application Laid-Open Publication No. 2010-48120, for example, discloses an actuator system. The proposed actuator system stores maximum and minimum resistance values observed when a current is passed through a shape memory alloy wire, and performs resistance control based on a resistance value of the shape memory alloy wire.

The above actuator system performs calibration at startup of the actuator system by detecting the minimum resistance value within the moving range of an actuator. A correction value resulting from the calibration is used to perform the resistance control.

SUMMARY OF THE INVENTION

An endoscope system in an aspect of the present invention is an endoscope system including an image pickup device picking up an image of an object and an objective optical system. The endoscope system includes: an actuator having a shape memory element and driving a moving member for moving the objective optical system; an actuator drive unit driving the actuator; a resistance value detection section detecting a resistance value of the shape memory element for detecting a position of the moving member; an instruction input unit to which an instruction to move the objective optical system is inputted; and a control section outputting a driving signal to the actuator drive unit on a basis of the instruction inputted to the instruction input unit and the position of the moving member corresponding to the resistance value detected by the resistance value detection section. In response to a moving instruction inputted to the instruction input unit to move the objective optical system from a first position to a second position, the control section outputs the driving signal so that a current for moving the moving member from the first position to a third position beyond the second position is passed through the shape memory element. When the moving member reaches the third position, the control section outputs the driving signal so that a first constant current is passed through the shape memory element until the resistance value of the shape memory element becomes a first resistance value smaller than a resistance value of the shape memory element corresponding to the third position and larger than a minimum resistance value within a moving range of the moving member. When the resistance value of the shape memory element becomes the first resistance value, the control section outputs the driving signal so that a first holding constant current smaller than the first constant current is passed through the shape memory element. When the resistance value of the shape memory element becomes a second resistance value larger than the first resistance value during passage of the first holding constant current through the shape memory element, the control section outputs the driving signal so that a current is passed through the shape memory element, the current being for holding the moving member at a position farther than the second position from the first position within a range in which the resistance value of the shape memory element does not reach the minimum resistance value.

A method for controlling an endoscope actuator in an aspect of the present invention is a method for controlling an endoscope actuator, the actuator having a shape memory element and driving a moving member for moving an objective optical system for an image pickup device picking up an image of an object, the actuator being controlled with: an actuator drive unit driving the actuator; a resistance value detection section detecting a resistance value of the shape memory element for detecting a position of the moving member; an instruction input unit to which an instruction to move the objective optical system is inputted; and a control section outputting a driving signal to the actuator drive unit on the basis of the instruction inputted to the instruction input unit and the position of the moving member corresponding to the resistance value detected by the resistance value detection section. In response to a moving instruction inputted to the instruction input unit to move the objective optical system from a first position to a second position, the control section outputs the driving signal to the actuator drive unit so that a current for moving the moving member from the first position to a third position beyond the second position is passed through the shape memory element. When the moving member reaches the third position, the control section outputs the driving signal to the actuator drive unit so that a first constant current is passed through the shape memory element until the resistance value of the shape memory element becomes a first resistance value smaller than a resistance value of the shape memory element corresponding to the third position and larger than a minimum resistance value within a moving range of the moving member. When the resistance value of the shape memory element becomes the first resistance value, the control section outputs the driving signal to the actuator drive unit so that a first holding constant current smaller than the first constant current is passed through the shape memory element. When the resistance value of the shape memory element becomes a second resistance value larger than the first resistance value during passage of the first holding constant current through the shape memory element, the control section outputs the driving signal to the actuator drive unit so that a current is passed through the shape memory element, the current being for holding the moving member at a position farther than the second position from the first position within a range in which the resistance value of the shape memory element does not reach the minimum resistance value.

BRIEF DESCRIPTION OF THE DRAWINGS

FIG. 9 is a table TBL summarizing a starting condition, a finishing condition, a control mode, and a driving current for each control according to the embodiment of the present invention.

DETAILED DESCRIPTION OF THE PREFERRED EMBODIMENT

Figure 1:
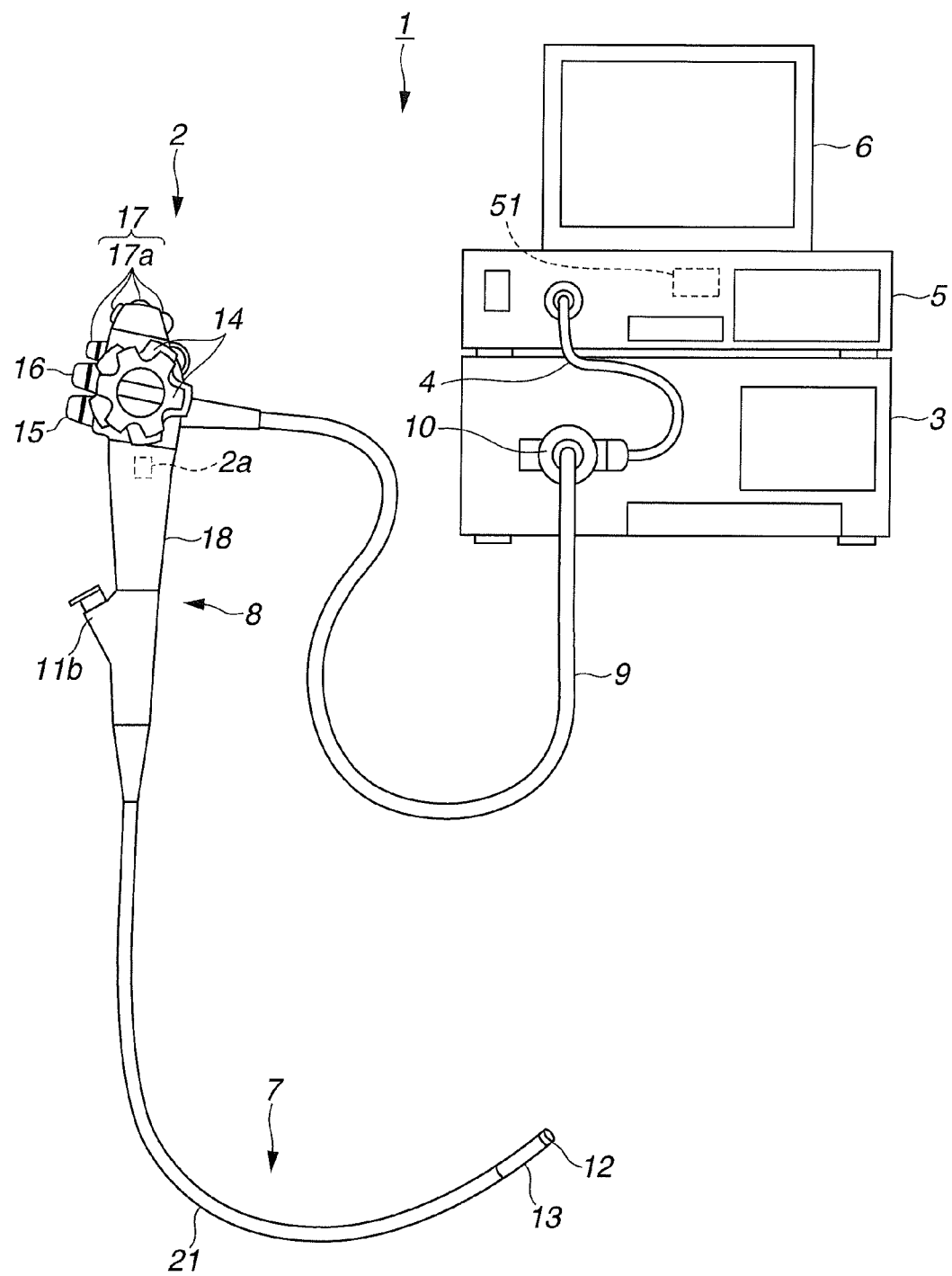
FIG. 1 is a configuration diagram showing a configuration of an endoscope system according to an embodiment of the present invention.

An embodiment of the present invention will be described with reference to the drawings.
(Overall Configuration)
First, a configuration of an endoscope system according to the present embodiment will be described with reference to FIG. 1, which is a configuration diagram showing the configuration of the endoscope system according to the present embodiment.

An electronic endoscope system (hereinafter simply referred to as an endoscope system) 1 in the present embodiment includes an electronic endoscope (hereinafter simply referred to as an endoscope) 2, a light source apparatus 3, a video processor (hereinafter referred to as a processor) 5, and a color monitor (hereinafter referred to as a monitor) 6, which are electrically connected.

The endoscope 2 has an insertion section 7, and an operation section 8 to which the insertion section 7 is extendedly coupled. A universal code 9 extending from the operation section 8 is connected to the light source apparatus 3 through a scope connector 10. An electric connector in one end portion of a scope cable 4 is detachably connected to the scope connector 10. An electric connector in the other end portion of the scope cable 4 is connected to the processor 5.

The insertion section 7 includes, from the distal end, a distal end portion 12, a bending portion 13, and a flexible tube portion 21, which are connected in series. A distal end opening, an observation window, two illuminating windows, an observation window cleaning mouth, and an observed object cleaning mouth are provided on a distal end face of the distal end portion 12.

On a rear side of the observation window in the distal end portion 12 of the insertion section 7, an image pickup apparatus embedded in the distal end portion 12 is provided. The image pickup apparatus includes an image pickup device which picks up an image of an object, and an objective optical system. A light guide bundle (not shown) is provided on a rear side of the two illuminating windows. The light guide bundle, extending from the distal end portion 12 into the universal code 9, transfers illuminating light from the light source apparatus 3.

The operation section 8 includes: a forceps opening 11b provided in a side portion on a lower side; a grip portion 18 in a middle portion; and two bending operation sections 14, an air and water supply control section 15, a suction control section 16, and a switch portion 17, provided on an upper side. The switch portion 17, including a plurality of switches 17a, is used mainly for operating image pickup functions.

Figure 2:
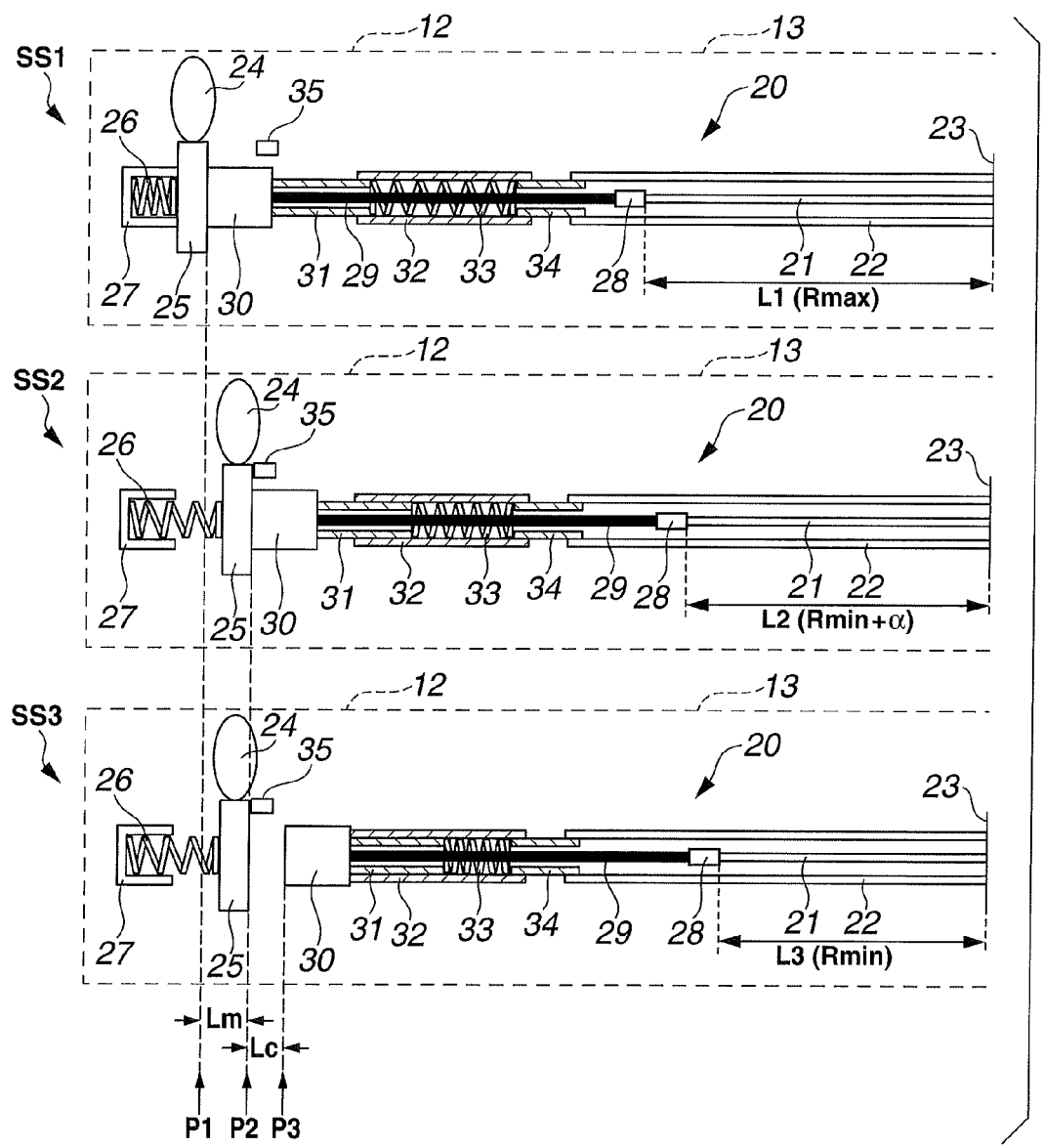
FIG. 2 is a diagram for describing a configuration of an actuator for an objective optical system according to the embodiment of the present invention.

The plurality of switches 17a include one or two switches for focus functions, constituting an instruction input unit for inputting an instruction to move the objective optical system.
(Configuration of Actuator in Distal End Portion)
FIG. 2 is a diagram for describing a configuration of an actuator for the objective optical system in the distal end portion 12 of the insertion section 7. An actuator 20 shown in FIG. 2 is provided on a distal end side of the insertion section 7. The actuator 20 has a shape memory element and drives a moving member for moving the objective optical system within the insertion section 7.

As shown in FIG. 2, a shape memory alloy (hereinafter abbreviated as SMA) wire 21, which is the shape memory element used by the actuator 20 for driving, has a diameter of several tens of μm (micrometers) and is inserted in a flexible tube 22. A proximal end portion of the SMA wire 21 is fixed to a fixing member 23 in the insertion section 7.

On the other hand, a lens 24, which is one objective optical system among a group of lenses of an observation optical system, is fixed to a lens frame 25. The lens 24 is moved with the movement of the lens frame 25. A first coil spring 26 is disposed between a spring fixing member 27 and the lens frame 25. The spring fixing member 27 is fixed to a distal-end rigid member (not shown) in the distal end portion 12 of the insertion section 7. With this configuration, the lens frame 25 is pressed toward a proximal end side of the insertion section 7 by the coil spring 26, which is an elastic member.

A distal end portion of the wire 21 is connected to one end of a stainless (SUS) wire 29 by a crimping member 28. The other end of the wire 29 is adhesively fixed to a moving member 30 that shuttles, i.e., moves, toward the lens frame 25. That is, the SMA wire 21 is connected to the moving member 30 through the wire 29. The SMA wire 21 is indirectly connected to the moving member 30 in order to prevent the image pickup device (not shown) provided in the distal end portion 12 of the insertion section 7 from being affected by heat produced by the SMA wire 21.

One end of a pipe 31 is fixedly connected to a proximal end portion of the moving member 30. The other end of the pipe 31 is inserted inside a distal end side of a pipe 32 and contacts a distal end portion of a second coil spring 33 inserted in the pipe 32. The pipe 32 is fixed to the distal-end rigid member (not shown). The pipe 31 is inserted in the pipe 32 slidably in the axis direction. The moving member 30, contacting the lens frame 25, is pressed toward the distal end side by the coil spring 33, which is an elastic member. The amount of spring force of the coil spring 33 is larger than that of the coil spring 26. The coil springs 26 and 33 are provided as compressed in the spring fixing member 27 and the pipe 32, respectively.

A proximal end portion of a pipe 34 is fixedly inserted in a distal end portion of the tube 22. A distal end portion of the pipe 34 is fixedly inserted in the pipe 32 on a proximal end side of the pipe 32. The distal end portion of the pipe 34 contacts a proximal end portion of the coil spring 33 inside the pipe 32.

The wire 29 is inserted in the internal space of the pipes 22, 31, 32, and 34, and the coil spring 33. The SMA wire 21 connected through the crimping member 28 is also inserted in the pipe 22. The SMA wire 21 has two terminal portions (not shown) provided therein, so that current can be passed through the SMA wire 21 via the two terminal portions, as will be described below.

A lens stopper 35 is fixedly provided in the distal-end rigid member. The lens stopper 35 is a member that butts the lens frame 25 to prevent the lens frame 25 from being moved beyond a predetermined lens position when the moving member 30 is moved toward the proximal end side.

In FIG. 2, a state SS1 illustrates a state in which no current is passed through the SMA wire 21. The SMA wire 21 is elongated in the tube 22 with some slack. The pipe 31 is pressed toward the distal end side due to the amount of spring force of the coil spring 33. Since the amount of spring force of the coil spring 33 trying to extend is larger than that of the coil spring 26 trying to extend, the pipe 31 presses the moving member 30 toward the distal end side. Then, the moving member 30 presses the lens frame 25 toward the distal end side, so that the lens frame 25 contacts the spring fixing member 27 to press the spring fixing member 27 toward the distal end direction. In the state SS1, a distal end of the moving member 30 is located at a first position P1. When the distal end of the moving member 30 is at the first position P1, the lens 24 fixed to the lens frame 25 is at a far-point focus position of the objective optical system.

In the state SS1, passing the current through the SMA wire 21 causes the SMA wire 21 to produce heat and start contraction. As the SMA wire 21 contracts, the slack of the wire 21 decreases and the force of pulling the wire 29 toward the proximal end side gradually increases. When the sum of the pulling force and the amount of spring force of the coil spring 26 exceeds the amount of spring force of the coil spring 33 trying to extend, the wire 29 coupled to the wire 21 is moved to the proximal end side.

When the lens frame 25 contacts the lens stopper 35 during the movement of the wire 29, the movement of the lens 24 toward the proximal end side is stopped, as illustrated as a state SS2 in FIG. 2. In the state SS2, the distal end of the moving member 30 is located at a second position P2. When the moving member 30 is at the second position P2, the lens 24 fixed to the lens frame 25 is at a near-point focus position of the objective optical system.

Continuously passing the current through the wire 21 after the lens frame 25 contacts the lens stopper 35 causes the SMA wire 21 to further produce heat and be contracted. Since the wire 29 is moved to the proximal end side due to the contraction of the SMA wire 21, the moving member 30 is also moved to the proximal end side. The moving member 30 contacts the distal end portion of the pipe 32 and stops (state SS3). In the state SS3, the distal end of the moving member 30 is located at a third position P3. Although the moving member 30 is moved from the second position P2 to the third position P3, the lens 24 fixed to the lens frame 25 remains at the near-point focus position because the lens stopper 35 stops the movement of the lens frame 25. In the state SS3, the lens frame 25 is standing still while pressed to the lens stopper 35 by the coil spring 26 toward the proximal end direction.

Even if the current is continuously passed through the SMA wire 21 after the moving member 30 contacts the distal end portion of the pipe 32 and is stopped, the SMA wire 21 cannot be contracted any more because the wire 29 is not elongated (state SS3).

Thus, controlling the current to the SMA wire 21 allows the distal end of the moving member 30 to be moved within the range of the difference between the first position P1 and the third position P3. However, as described above, the operation range of the lens frame 25 (i.e., the operation range of the lens 24) is between the first position P1 and the second position P2.

The distal end side of the insertion section 7 of the endoscope 2 has the bending portion 13. The tube 22 bends by the influence of a bending operation of the bending portion 13. Due to the tension applied to the SMA wire 21 and the wire 29 to make the wires contracted as described above, the wires always try to be linear. Since the SMA wire 21 and the wire 29 are thin, the wires can move orthogonally to the axis within the tube 22 and the pipes 31, 32, and 34. Therefore, when the tube 22 bends, the SMA wire 21 and the wire 29 do not take the same bending shape as the tube 22. As a result, when the distal end of the moving member 30 is at the third position P3, bending of the tube 22 may cause a phenomenon that the moving member 30 is pushed toward the distal end side, due to the difference between the radius of curvature of the tube 22 and the radius of curvature of the wires 21 and 29 (hereinafter referred to as a radius-of-curvature difference).

For this reason, a clearance region Lc is provided in advance in order to prevent the moving member 30 from moving the lens frame 25 even if a bending operation causes the moving member 30 to be pushed toward the distal end side. The clearance region Lc ranges between the position P2 and the position P3. The clearance region Lc is set to be not smaller than the amount of movement of the moving member 30 due to the radius-of-curvature difference.

Here, if the current value of the current supplied to the SMA wire 21 is reduced in the state SS3, the distal end of the moving member 30 is moved toward the position P2. If the current value of the supply current to the SMA wire 21 is reduced further or is reduced to zero, the distal end of the moving member 30 is moved beyond the position P2 to the position P1 and returns. As a result, the lens 24 comes to the far-point focus position.

Thus, the range between the position P1 and the position P2 is the lens operation range, i.e., a lens operation region Lm, and the range between the position P2 and the position P3 is a clearance range, i.e., the clearance region Lc.

Figure 3:
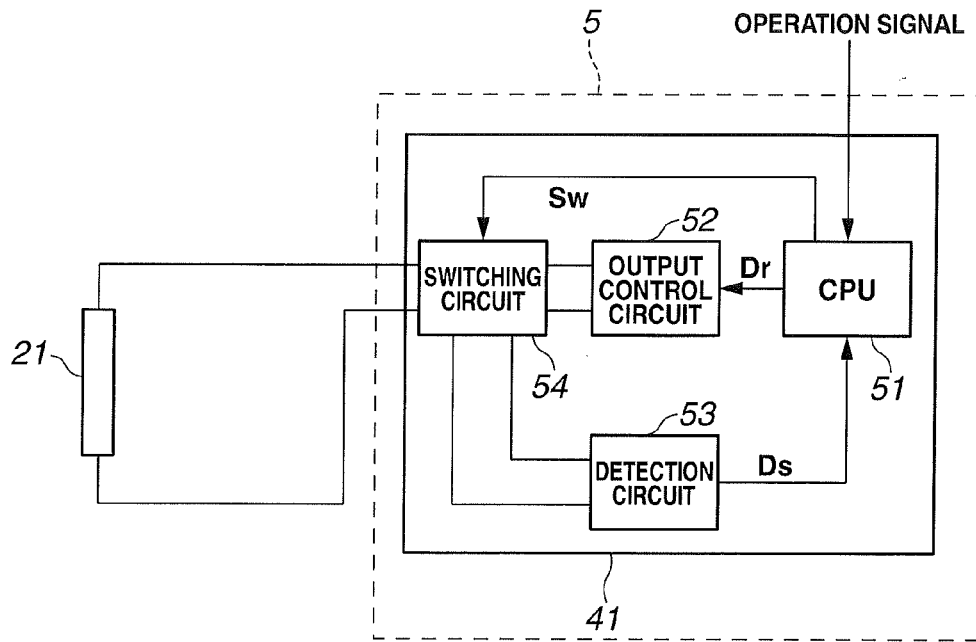
FIG. 3 is a block diagram showing a configuration of a control circuit for controlling elongation and contraction of an SMA wire 21 according to the embodiment of the present invention.

FIG. 3 is a block diagram showing a configuration of a control circuit for controlling elongation and contraction of the SMA wire 21. A control circuit 41 is included in the processor 5. It is to be noted that FIG. 3 shows only the control circuit for controlling elongation and contraction of the SMA wire 21 in the processor 5. The control circuit 41 includes a central processing unit (hereinafter referred to as a CPU) 51 serving as a control section, an output control circuit 52 serving as an actuator drive unit, a detection circuit 53 serving as a resistance value detection section, and a switching circuit 54. The SMA wire 21 is connected to the switching circuit. The output control circuit 52 constitutes the actuator drive unit that drives the actuator 20. The detection circuit 53 constitutes the resistance value detection section that detects the resistance value of the SMA wire 21 for detecting the position of the moving member 30.

The CPU 51 serving as the control section responds to a user's operation on the switches 17a in the operation section 8 to perform driving control for the actuator 20 according to a control program (not shown).

The CPU 51 supplies a driving signal Dr to the output control circuit 52, which outputs a current signal to the switching circuit 54. The CPU 51 also controls the supply current to the SMA wire 21 by repeating a basic control interval including a heating control period and a resistance value detection period. That is, the CPU 51 supplies a switching signal Sw to the switching circuit 54 so that the heating control period T1 and the resistance value detection period T2 alternate. Accordingly, the switching circuit 54 is switched to output the current signal from the output control circuit 52 to the SMA wire 21 during the heating control period T1, and to supply a predetermined resistance detection voltage to the SMA to detect the resistance value of the SMA wire 21 from a voltage drop value occurring at the both ends of the SMA wire 21 during the resistance value detection period T2.

For example, the basic control interval may be 12 milliseconds, in which the first 10 milliseconds may be the heating control period T1 and the following 2 milliseconds may be the resistance value detection period T2. The current to the SMA wire 21 is intermittently supplied or stopped only during the heating control period T1, and the resistance value of the SMA wire 21 is also intermittently detected, i.e., measured, during the resistance value detection period T2.

The basic control interval, the heating control period T1, and the resistance value detection period T2 are not limited to the values illustrated above but may have values of, for example, 6 milliseconds, 5 milliseconds, and 1 millisecond, respectively.

Thus, when the lens 24 is driven to the near-point focus position in response to operation of a certain switch in the operation section 8, the CPU 51 supplies a predetermined driving current to the SMA wire 21 during the heating control period T1, and supplies a predetermined detection current to the SMA wire 21 to detect the resistance value of the SMA wire 21 during the resistance value detection period T2. The detection circuit 53 supplies the detected resistance value as a detection signal Ds to the CPU 51.

When movement of the lens 24 to the far-point focus position is instructed with a certain switch in the operation section 8, the CPU 51 refrains from supplying the predetermined driving current to the SMA wire 21 during the heating control period T1, and supplies a predetermined resistance detection voltage to the SMA wire 21 to detect the resistance value of the SMA wire 21 during the resistance value detection period T2. Since the heating current is not supplied, the SMA wire 21 cannot be contracted and the lens 24 is moved to the far-point focus position.

(Calibration Process)

A process of measuring and storing a minimum resistance value and a maximum resistance value of the SMA wire 21 will be described. In the present embodiment, the position of the lens 24 is controlled by controlling the current supplied to the SMA wire 21 with reference to the resistance value of the SMA wire 21. When the SMA wire 21 is not heated, the actuator is in the state SS1. In the state SS1, the unheated SMA wire 21 has a maximum length L1, and the resistance value at this point is a maximum resistance value Rmax. When the SMA wire 21 is heated and the actuator is in the state SS3, the SMA wire 21 has a minimum length L3, and the resistance value at this point is a minimum resistance value Rmin In the state SS2, the SMA wire 21 has a length L2, and the resistance value at this point is (Rmin+α). The lens 24 is moved within the range between the maximum resistance value Rmax and the resistance value (Rmin+α).

The minimum resistance value Rmin and the maximum resistance value Rmax vary among actuators due to reasons such as variations in the wire diameter of the SMA wire 21, variations in the wire length occurring at the time of cutting, and variations in the setup dimensions occurring at the time of assembly as an actuator. Therefore, the minimum resistance value Rmin and the maximum resistance value Rmax are characteristic values unique to each actuator. These characteristic values are measured in a calibration process at the time of factory shipment. Alternatively, the calibration process may be performed after the factory shipment, before the user starts using the endoscope.

The minimum resistance value Rmin and the maximum resistance value Rmax measured in the calibration process are stored in a nonvolatile memory 2a provided in the endoscope 2. In FIG. 1, the nonvolatile memory 2a is located in the operation section 7.

Figure 4:
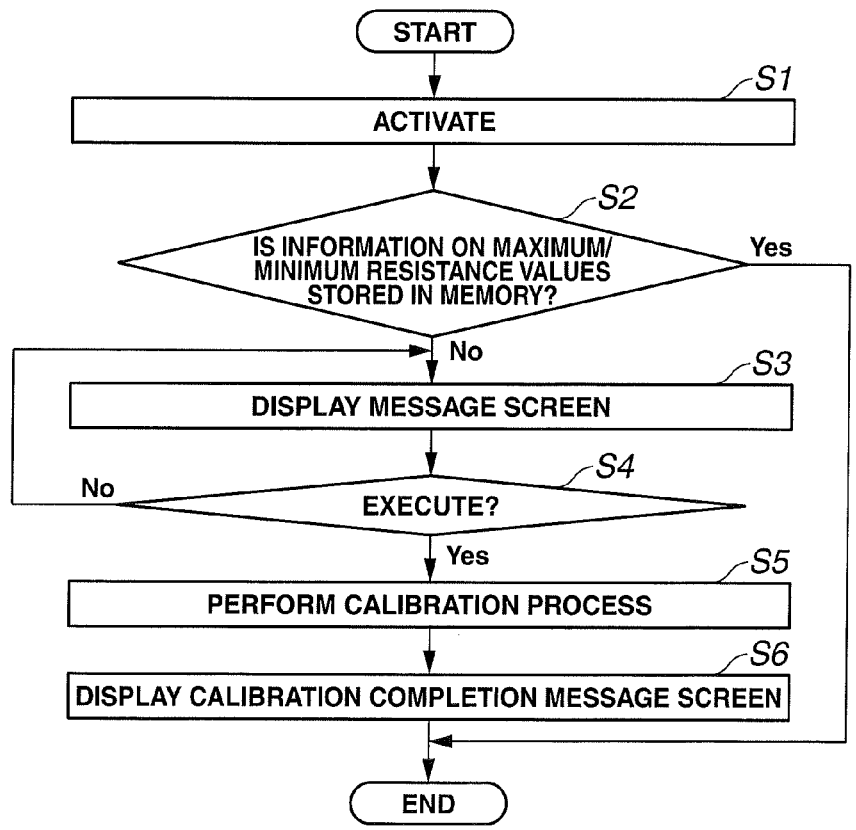
FIG. 4 is a flowchart showing a flow of a calibration process according to the embodiment of the present invention.

FIG. 4 is a flowchart showing a flow of the calibration process. The process is performed before the factory shipment when the processor 5 is activated, or after the factory shipment when the processor 5 is activated by the user, while the processor 5 is connected with the endoscope 2.

In response to a power button (not shown) turned on, the CPU 51 performs an activation process for the processor 5 (S1). After the activation process, the CPU 51 determines whether or not information on the minimum resistance value Rmin and the maximum resistance value Rmax of the memory wire 21 is stored in the memory 2a of the endoscope 2 (S2). The CPU 51 makes this determination by reading data in a predetermined storage region in the memory 2a. If the information on the minimum resistance value Rmin and the maximum resistance value Rmax is stored in the memory 2a (S2: YES), the process terminates with no further operation.

Figure 5:
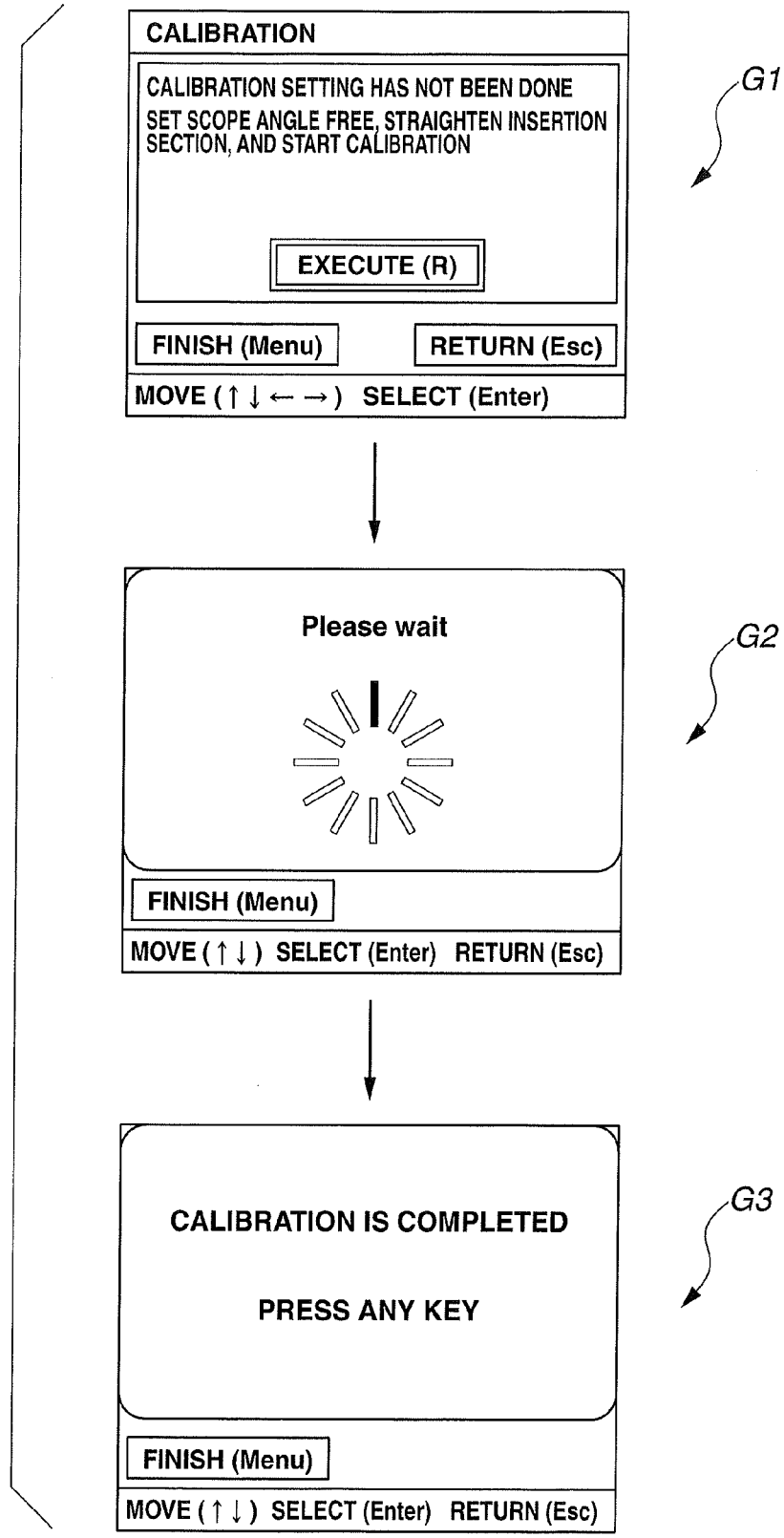
FIG. 5 is a diagram showing transitions of a screen displayed on a monitor 6 in the calibration process according to the embodiment of the present invention.

If the information on the minimum resistance value Rmin and the maximum resistance value Rmax is not stored in the memory 2a (S2: NO), the CPU 51 displays a predetermined message screen on the monitor 6 (S3). FIG. 5 is a diagram showing transitions of the screen displayed on the monitor 6 in the calibration process. A screen G1 in FIG. 5 is an exemplary screen displayed as a result of the process of S3. The screen G1 displays a message informing that the minimum resistance value Rmin and the maximum resistance value Rmax have not been set by the calibration, and also displays an "execute" button for outputting a calibration execution command. A shipment inspector or the user may move a cursor on the screen and select the "execute" button to instruct the CPU 51 to perform the calibration.

After S3, it is determined whether or not the calibration is instructed (S4). If the calibration is not instructed (S4: NO), the process returns to S3.

If the execution is instructed (S4: YES), the CPU 51 performs the calibration process (S5). In the calibration process, with the insertion section 7 straightened, the resistance value of the SMA wire 21 before the current is passed through the wire 21 is measured to obtain data on the maximum resistance value Rmax. Then, the current is passed through the SMA wire 21, and when the moving member 30 is at the position P3, the resistance value of the SMA wire 21 is measured to obtain data on the minimum resistance value Rmin During the process of S5, the CPU 51 displays a screen G2 in FIG. 5 on the monitor 6. The screen G2 displays a message asking the user or the like to wait for a while because the calibration process is ongoing.

Upon completion of the process of S5, the CPU 51 displays a calibration completion message screen on the monitor 6 (S6). A screen G3 in FIG. 5 is an exemplary calibration completion message screen. The screen G3 includes a message that the calibration is completed.

In the above manner, the calibration process is performed in which the data on the minimum resistance value Rmin and the maximum resistance value Rmax is obtained and stored in the memory 2a.

At the time of using the endoscope system, the data on the minimum resistance value Rmin and the maximum resistance value Rmax stored in the memory 2a is read by the CPU 51 from the memory 2a, and used for focus control to be described below.

Since the minimum resistance value Rmin and the maximum resistance value Rmax are unique values for the actuator 20 inside the endoscope 2, these values are stored in the memory 2a provided in the endoscope 2. The memory 2a may also store other values used in the focus control to be described below, such as parameters for setting target resistance values, an upper-limit current value, current values of constant currents, and parameters for changing the constant currents.

(Focus Switching Control)

The focus control in the endoscope 2 is control between two positions, i.e., the near-point focus position and the far-point focus position. With reference to an object image displayed on the monitor 6 of the endoscope 2, the user can set the focus position for the object image to either the near-point focus position or the far-point focus position by operating a certain one of the plurality of operation switches 17a in the operation section 8. When the far-point focus position is selected, the SMA wire 21 is elongated with no current passed through the SMA wire 21. When the near-point focus position is selected, the SMA wire is contracted with the current passed through the SMA wire 21.

The CPU 51 constitutes the control section that outputs the driving signal Dr to the output control circuit 52, on the basis of the instruction inputted with one of the plurality of switches 17a serving as the instruction input unit, and on the basis of the position of the moving member 30 corresponding to the resistance value detected by the detection circuit 53.

(Control for Near-Point Focus Position)

Figure 6:
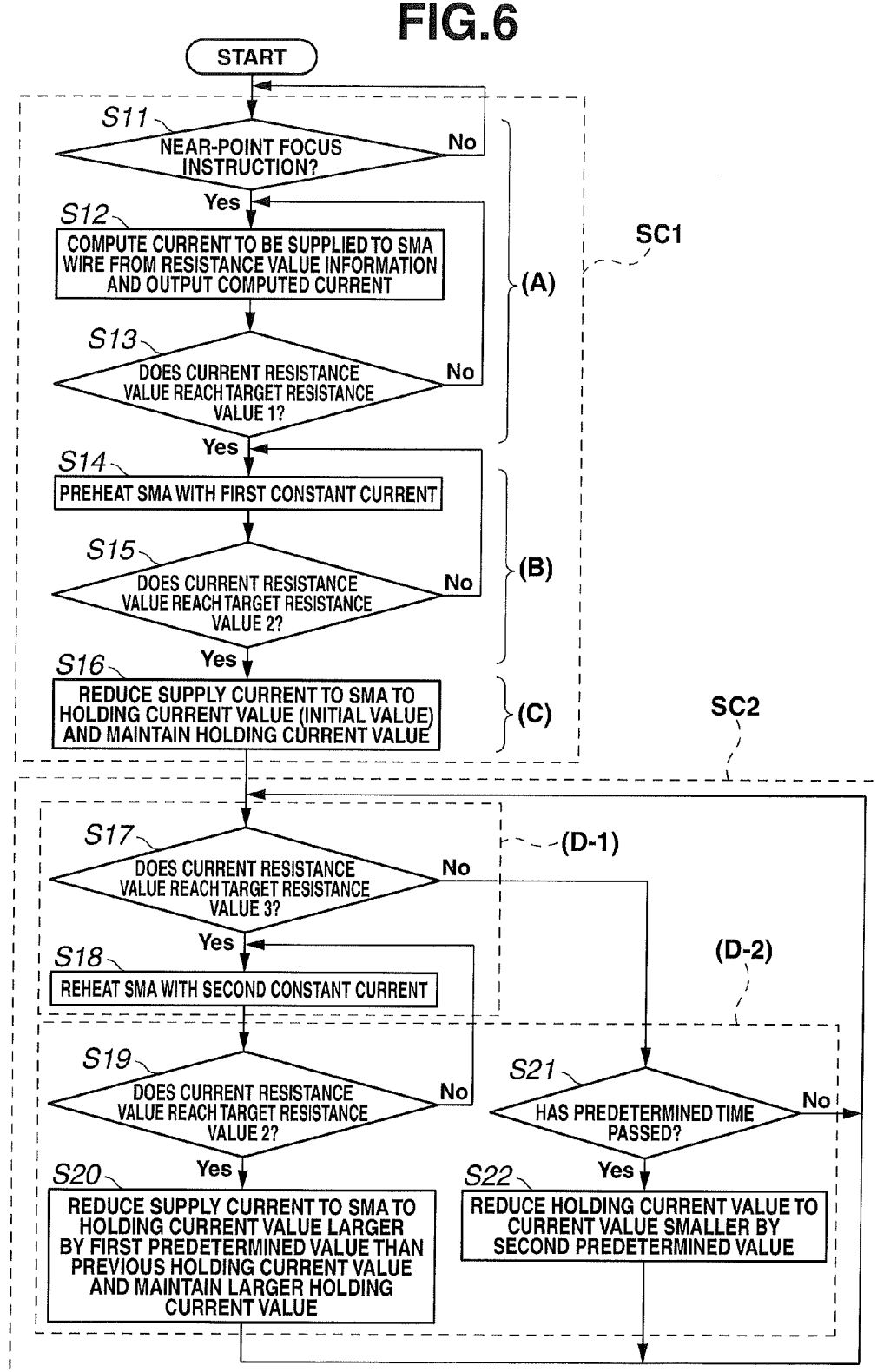
FIG. 6 is a flowchart showing a flow of control for switching to a near-point focus position according to the embodiment of the present invention.
Figure 7:
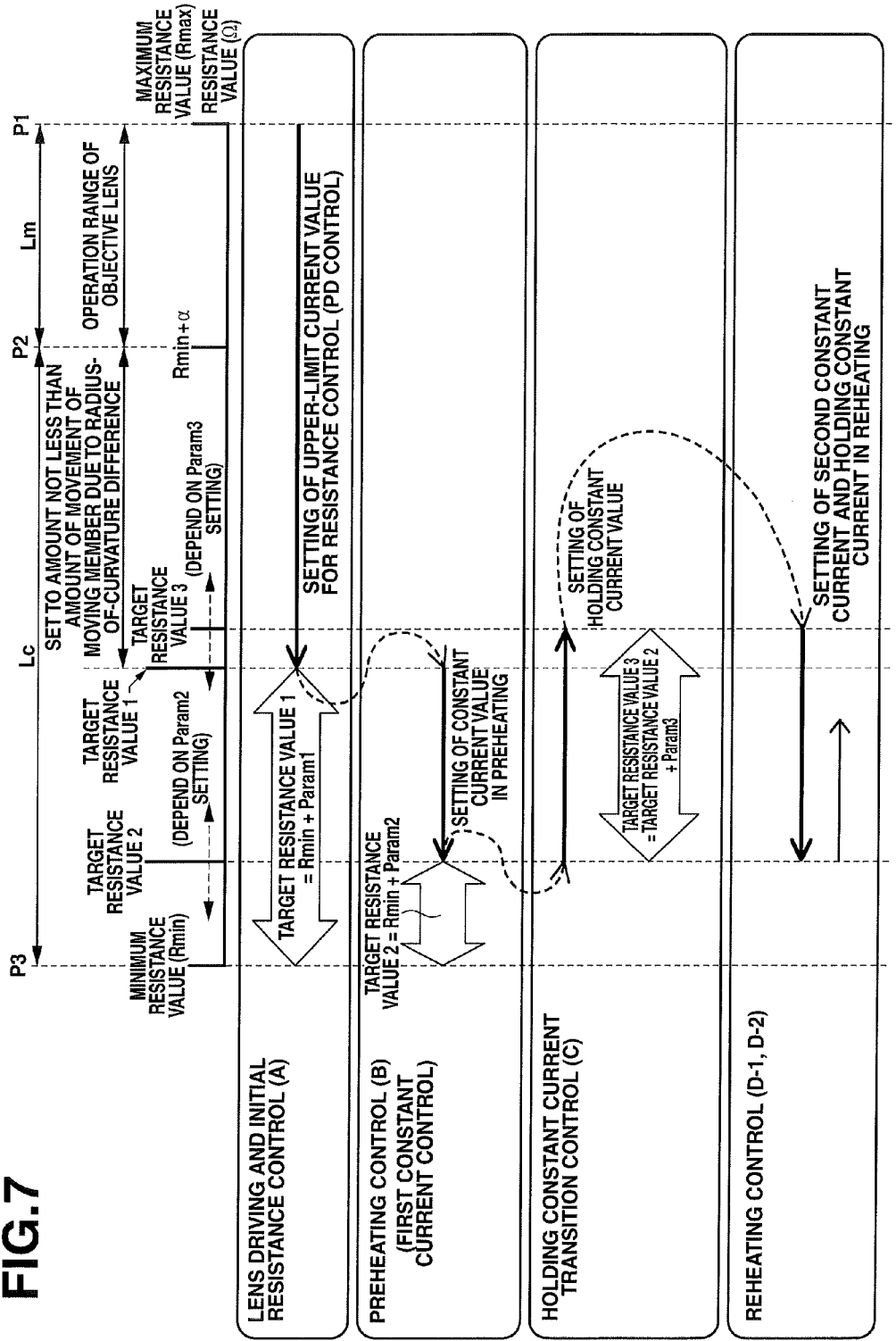
FIG. 7 is a diagram for describing a minimum resistance value Rmin, a maximum resistance value Rmax, and target resistance values, and details of their associated processes according to the embodiment of the present invention.
Figure 8:
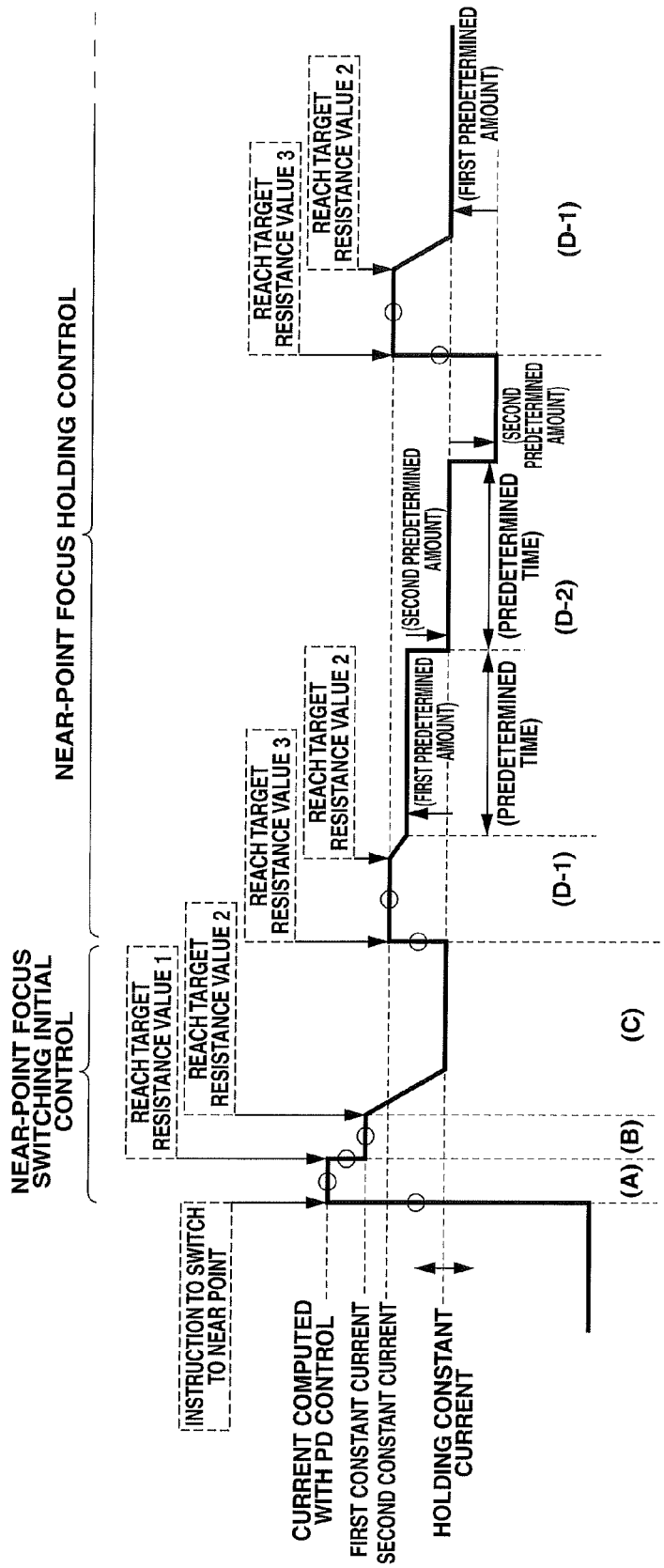
FIG. 8 is a diagram showing changes over time in supply current to the SMA wire 21 according to the embodiment of the present invention.

FIG. 6 is a flowchart showing a flow of control for switching to the near-point focus position. FIG. 7 is a diagram for describing the minimum resistance value Rmin, the maximum resistance value Rmax, and target resistance values, and details of their associated processes. FIG. 8 is a diagram showing changes over time in supply current to the SMA wire 21. The control for the near-point focus position is largely divided into near-point focus switching initial control SC1 and near-point focus holding control SC2. Upon a near-point focus instruction, the main control status enters the near-point focus switching initial control SC1 and then moves to the near-point focus holding control SC2.

(Near-Point Focus Switching Initial Control SC1)

The CPU 51 determines whether or not the user provides a near-point focus instruction (S11). If the near-point focus instruction is not provided (S11: NO), no processing is performed.

If the near-point focus instruction is provided (S11: YES), the CPU 51 serving as the control section computes a current value of the current to be supplied to the SMA wire from resistance value information, and outputs the driving signal Dr for supplying the current at the computed current value (S12). Specifically, the CPU 51 computes the current value of the current to be passed through the SMA wire 21 from information on the resistance value of the wire 21 detected by the detection circuit 53 and information on a predetermined target resistance value 1. The CPU 51 supplies the driving signal Dr to the output control circuit 52 so that the computed current is outputted during the above-described heating control period T1.

The target resistance value 1 is a resistance value obtained by adding a predetermined parameter Param1 to the minimum resistance value Rmin, as shown in FIG. 7. The SMA wire 21 has a predetermined relationship between the resistance value and the wire length. Further, the SMA wire 21 has a predetermined relationship between the applied current and the resistance value. This relationship has what is called hysteresis characteristics: the relationship between the current value and the resistance value differs between a case where the elongated SMA wire 21 is contracted with the current applied thereto and a case where the contracted SMA wire 21 is elongated with the amount of the applied current reduced.

The target resistance value 1 is changeable by changing the parameter Param1.

The target resistance value 1 in S12 is preset with consideration for the hysteresis characteristics. Further, the target resistance value 1 is a resistance value corresponding to a predetermined position of the moving member 30 in the clearance region Lc.

Specifically, as shown in FIG. 7, the target resistance value 1 is set to a resistance value corresponding to a position not less than the moving amount of the moving member 30 due to the radius-of-curvature difference in the clearance region Lc, beyond the lens operation region Lm between the positions P1 and P2, which is the operation range of the objective lens 24.

Here, the current value of the current to be applied to the SMA wire 21 is determined with PD (proportional-plus-derivative) control computation based on the resistance value of the wire 21 detected by the detection circuit 53 and based on the predetermined target resistance value 1. Specifically, with the PD (proportional-plus-derivative) control based on the resistance value detected by the detection circuit 53 and the resistance value corresponding to the position of the target resistance value 1 of the SMA wire 21, the CPU 51 performs control for heating the SMA wire 21 by passing the current through the SMA wire 21 for moving the moving member 30 from the position P1 to the position of the target resistance value 1. In order to prevent passing a current not smaller than a certain current value during the PD control, an upper-limit current value is predetermined The supply current is limited so that the current value of the supply current to the SMA wire 21 does not exceed the upper-limit current value.

It is then determined whether or not the current resistance value of the wire 21 detected by the detection circuit 53 reaches the target resistance value 1 (S13). If the current resistance value does not reach the target resistance value 1, the process returns to S12. The process from S11 to S13 constitutes initial resistance control (A).

In the initial resistance control (A), the CPU 51 responds to the instruction inputted to the operation section 8 serving as the instruction input unit, instructing to move the lens 24 from the far-point position P1 to the near-point position P2. The CPU 51 then outputs the driving signal Dr so that the current for moving the moving member 30 from the far-point position P1 through the near-point position P2 to the position corresponding to the target resistance value 1 is passed through the SMA wire 21 to heat the SMA wire 21.

Thus, when the lens 24 is driven to the near-point focus position, with the initial resistance control (A) in FIG. 7, the current is supplied to the SMA wire 21 while the heating period with the current supply and the resistance value detection period alternate.

If the current resistance value of the wire 21 detected by the detection circuit 53 reaches the target resistance value 1, the CPU 51 preheats the SMA wire 21 with a first constant current (S14). Specifically, the CPU 51 outputs the driving signal Dr for constant current control in which a constant current at a first constant current value is supplied to the SMA wire 21.

It is determined whether or not the current resistance value of the wire 21 detected by the detection circuit 53 reaches a target resistance value 2 (S15). If the current resistance value does not reach the target resistance value 2, the process returns to S14. The target resistance value 2 is a value obtained by adding a predetermined parameter Param2 to the minimum resistance value Rmin The value of the parameter Param2 is smaller than the value of the parameter Param1. The processes of S14 and S15 constitute preheating control (B).

In the preheating control (B), the CPU 51 outputs the driving signal Dr so that the first constant current is passed through the SMA wire 21 to heat the SMA wire 21 until the resistance value of the SMA wire 21 reaches the target resistance value 2, which is larger than the minimum resistance value Rmin of the SMA wire 21.

The target resistance value 2 is changeable by changing the parameter Param2.

Thus, after the initial resistance control (A) in FIG. 7, the preheating control (B) is performed, in which the SMA wire 21 is preheated until the current resistance value becomes the target resistance value 2 while, again, the heating period with the supply of the first constant current and the resistance detection period alternate.

Here, the reason for not using only the PD control to bring the SMA wire 21 to the target resistance value 2 is to prevent the influence of vibrations caused by the responsiveness of the SMA wire 21 from extending to the lens operation range Lm.

Further, in the preheating control (B), the target resistance value 2 is not set to the minimum resistance value Rmin. This is because the durability of the SMA wire 21 would be decreased if the wire 21 were contracted to the minimum resistance value Rmin. For this reason, the target resistance value 2 is not set to the minimum resistance value Rmin If the current resistance value of the wire 21 detected by the detection circuit 53 reaches the target resistance value 2, the CPU 51 outputs the driving signal Dr so that the supply current to the SMA wire 21 is reduced to a holding current (initial value) and the holding current value is maintained (S16). The process of S16 constitutes a holding constant current transition control (C).

Once the resistance value of the SMA wire 21 becomes the target resistance value 2, the CPU 51 moves to the holding constant current transition control (C). The CPU 51 outputs the driving signal Dr so that the current value of the current passed through the SMA wire 21 is reduced to a second current value smaller than the current value of the first constant current.

In this holding constant current transition control (C), the constant current is supplied until the current becomes the holding current (initial value) while, again, the heating period with the supply of the constant current value and the resistance value detection period alternate.

The initial resistance control (A), the preheating control (B), and the holding constant current transition control (C) described above constitute the near-point focus switching initial control SC1. That is, the near-point focus switching initial control SC1, which is one of the main controls, includes the three sub controls: the initial resistance control (A), the preheating control (B), and the holding constant current transition control (C).

An example of changes in current value of the supply current to the SMA wire 21 up to this point will be described. As shown in FIG. 8, upon an instruction to switch to the near-point focus, the initial resistance control (A) is performed with the current value computed under the PD control. In a current waveform in FIG. 8, a line segment marked with ○ indicates a period in which the SMA wire 21 is actively heated, whereas a line segment not marked with ○ indicates a period in which the amount of heating for the SMA wire 21 is reduced or adjusted.

When the resistance value reaches the target resistance value 1, the preheating control (B) is performed for the constant current control with the first constant current value.

When the resistance value reaches the target resistance value 2, the holding constant current transition control (C) with the initial value is performed, in which holding constant current control is performed after the supply current is reduced to the holding current value.

After the near-point focus switching initial control SC1, the CPU 51 performs a reheating process. That is, while the first holding current of the second current value is passed through the SMA wire 21, the resistance value of the SMA wire 21 becomes a target resistance value 3. Then, the CPU 51 outputs a driving signal Dr for reheating the SMA wire 21 by passing, through the SMA wire 21, a current for holding the moving member 30 at a position farther than the near-point position P2 from the far-point position P1, within a range in which the resistance value of the SMA wire 21 does not reach the minimum resistance value Rmin (Near-Point Focus Holding Control SC2)

Returning to FIG. 6, it is determined whether or not the current resistance value reaches a target resistance value 3 (S17). If the current resistance value does not reach the target resistance value 3 (S17: NO), the process goes to S21. The target resistance value 3 is a value obtained by adding a predetermined parameter Param3 to the target resistance value 2.

As shown in FIG. 7, the target resistance value 3 is slightly larger than the target resistance value 1, but sufficiently larger than the resistance value (Rmin+α) corresponding to the position P2.

The target resistance value 3 is changeable by changing the parameter Param3.

If the current resistance value of the SMA wire 21 detected by the detection circuit 53 reaches the target resistance value 3 (S17: YES), the CPU 51 reheats the SMA wire 21 with a second constant current (S18). Specifically, the CPU 51 outputs the driving signal Dr for constant current control in which a constant current at the second constant current value is supplied to the SMA wire 21. Here, the current value of the second constant current is smaller than the current value of the first constant current.

The reheating causes the SMA wire 21 to be contracted again, and the resistance value begins to decrease.

It is then determined whether or not the current resistance value of the wire 21 detected by the detection circuit 53 reaches the target resistance value 2 (S19). If the current resistance value does not reach the target resistance value 2, the process returns to S18. The processes of S17 and S18 constitute reheating control (D-1) during holding. If the current resistance value of the wire 21 detected by the detection circuit 53 reaches the target resistance value 2 (S19: YES), the CPU 51 reduces the supply current to the SMA wire 21 to the holding current. That is, the CPU 51 reduces the current value of the supply current to a holding current value larger by a first predetermined value than the previous or initial holding current value, i.e., increased by the first predetermined value. The CPU 51 outputs the driving signal Dr so that the holding constant current at the reduced holding current value is outputted (S20).

This is for reducing the number of occurrences of the reheating (D), for example at a low ambient temperature. The process then moves to S17.

Once the current value of the holding constant current is outputted in S20, the current value is stored in RAM (not shown). Thereafter, when S20 is performed again or when S22 to be described below is performed during the near-point focus holding control SC2, the CPU 51 can refer to the previous current value of the holding constant current stored in the RAM.

It is determined whether or not the current resistance value reaches the target resistance value 3 in S17. If the current resistance value does not reach the target resistance value 3 (S17: NO), it is determined whether or not a predetermined time has passed (S21). The predetermined time, which is preset, is the time which has passed since the start of outputting of the holding constant current.

If the predetermined time has not passed in S21 (S21: NO), the process returns to S17.

If the predetermined time has passed in S21 (S21: YES), the current value of the holding current is reduced by a second predetermined value, and the reduced holding current is maintained (S22). That is, if it has taken the predetermined time or more for the resistance value of the SMA wire 21 to become the target resistance value 3 after the start of passing the above-described holding constant current through the SMA wire 21 in the reheating, the CPU 51 reduces the current value of the holding constant current by the second predetermined value. After S22, the process returns to S17.

This is for reducing the value of the holding constant current, such as at a high ambient temperature. The processes from S19 to S22 constitute holding current changing control (D-2).

In the reheating control in S18, the constant current is supplied while, again, the heating period with the supply of the constant current value and the resistance value detection period alternate.

The reheating control (D-1) during holding and the holding current changing control (D-2) described above constitute the near-point focus holding control SC2. That is, the near-point focus holding control SC2, which is one of the main controls, includes the two sub controls: the reheating control (D-1) during holding and the holding current changing control (D-2).

An example of changes in current value of the supply current to the SMA wire 21 up to this point will be described.

As shown in FIG. 8, when the resistance value of the SMA wire 21 decreases from the target resistance value 3 to the target resistance value 2 with the reheating control (D-1), the supply current to the SMA wire 21 is reduced to the holding current value larger by the first predetermined value than the previous holding current value with the holding current changing control (D-2). The supply current is thereafter maintained at the holding current value larger by the first predetermined value than the previous holding current value.

Thereafter, when the predetermined time has passed (S21: YES), the supply current to the SMA wire 21 is reduced by the second predetermined value (S22). In FIG. 8, thereafter, the current resistance value reaches the target resistance value 3 before the predetermined time passes.

Further, the reheating control (D-1) is performed. When the resistance value of the SMA wire 21 decreases from the target resistance value 3 to the target resistance value 2, the supply current to the SMA wire 21 is reduced to the previous holding current value. The supply current is thereafter maintained at the previous holding current value. The supply current to the SMA wire 21 is then changed with the holding current changing control (D-2).

Thus, with the processes of S19 and S20 in the holding current changing control (D-2), when the ambient temperature is low, the temperature of the actuator 20 can be increased early to lengthen the time it takes for the resistance value of the SMA wire 21 to decrease to the target resistance value 3. This allows the number of occurrences of the reheating to be reduced.

Also, with the processes of S21 and S22 in the holding current changing control (D-2), when the ambient temperature is high, the current value of the holding current is reduced as much as possible to save power.

Thus, in the near-point focus holding control SC2, the CPU 51 repeats: heating the SMA wire 21 by passing the second constant current through the SMA wire 21 until the resistance value of the SMA wire 21 becomes the target resistance value 2; and, when the resistance value of the SMA wire 21 becomes the target resistance value 2, reducing the current passed through the SMA wire 21 to the holding current value smaller than the current value of the second constant current. The CPU 51 thereby reheats the SMA wire 21 so that the moving member 30 is held at a position farther than the near-point position P2 from the far-point position P1.

FIG. 9 is a table TBL summarizing a starting condition, a finishing condition, a control mode, and a driving current for each of the above-described control.

As shown in the table TBL, for the initial resistance control (A) in the near-point focus switching initial control SC1, the starting condition is an instruction to switch to the near point, the finishing condition is reaching the target resistance value 1, the control mode is the PD (proportional-plus-derivative) control, and the driving current is the current value computed in the PD control.

For the preheating control (B), the starting condition is reaching the target resistance value 1, the finishing condition is reaching the target resistance value 2, the control mode is the constant current control, and the driving current is the first constant current.

For the holding constant current transition control (C), the starting condition is reaching the target resistance value 2, the finishing condition is reaching the target resistance value 3, the control mode is the constant current control, and the driving current is the holding constant current (initial value).

For the reheating control (during holding) (D-1) in the near-point focus holding control SC2, the starting condition is reaching the target resistance value 3, the finishing condition is reaching the target resistance value 2, the control mode is the constant current control, and the driving current is the second constant current.

For the holding current changing control (D-2), the starting condition is reaching the target resistance value 2, the finishing condition is reaching the target resistance value 3, the control mode is the constant current control (variable), and the driving current is the constant current of the current value changed by the predetermined value from the previous holding current.

Figure 10:
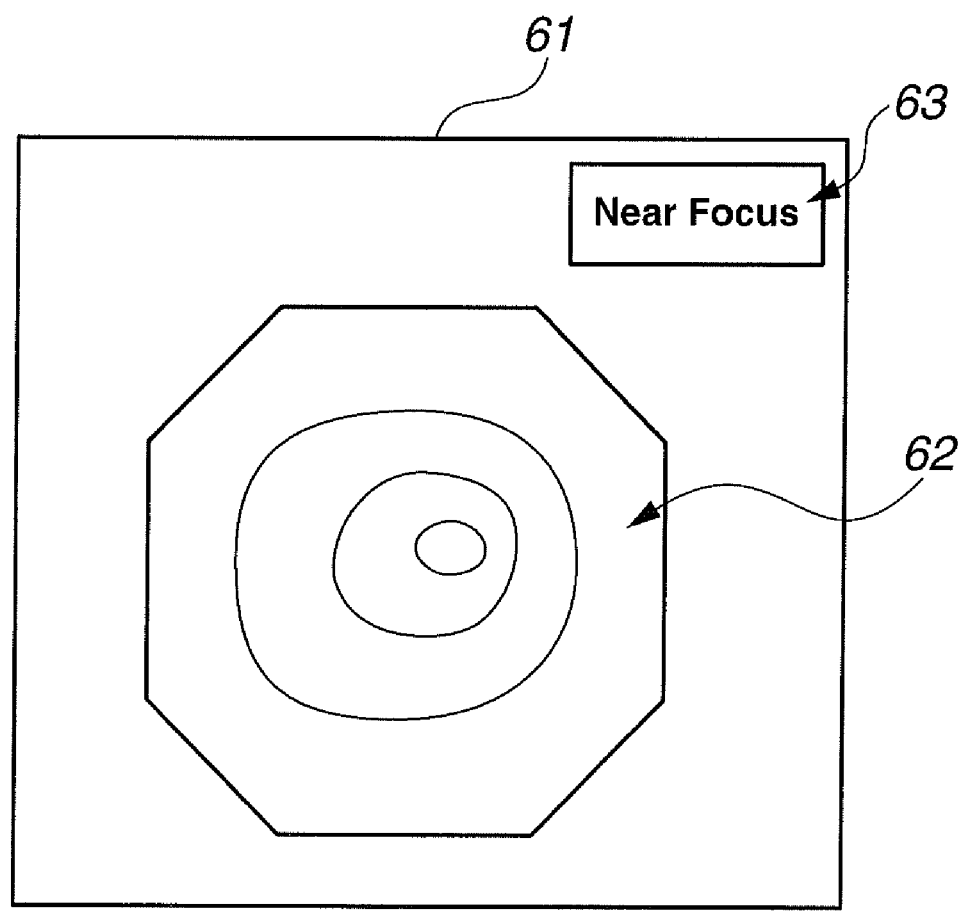
FIG. 10 is a diagram showing an exemplary display on the monitor of the endoscope system according to the embodiment of the present invention.

FIG. 10 is a diagram showing an exemplary display on the monitor of the endoscope system.

Once the focus position is switched to the near-point focus position, a display screen 61 of the monitor 6 displays a near-point state display portion 63 containing a display "Near Focus", indicating that an endoscope image 62 on the monitor 6 is a near-point focus image. The depth of field of an image differs between the near-point focus state and the far-point focus state. The observer can know or confirm that the depth of field of the endoscope image 62 is shallow at the time of near-point focus.

Thus, according to the control in the above-described embodiment, in response to an instruction to switch from the far-point focus position to the near-point focus, the CPU 51 performs the initial resistance control (A): the SMA wire 21 is heated and contracted to the target resistance value 1, which is larger than the minimum resistance value Rmin, with the PD control.

The moving member 30 is swiftly moved to the position corresponding to the target resistance value 2 with the initial resistance control (A). During the movement, the lens 24, which is the objective lens, is also swiftly moved to the near-point focus position.

When the resistance value of the SMA wire 21 becomes the target resistance value 1, the control is changed from the initial resistance control (A) to the preheating control (B).

The SMA wire 21 of the SMA wire 21 is further heated and contracted through the constant current control with the first constant current value in the preheating control (B). When the resistance value of the SMA wire 21 becomes the target resistance value 2, the control is changed from the preheating control (B) to the holding constant current transition control (C).

The target resistance value 2 is larger than the minimum resistance value Rmin Therefore, in the preheating control (B), the SMA wire 21 is not contracted up to a point at which the resistance value of the SMA wire 21 becomes the minimum resistance value Rmin This prevents decrease of the durability of the SMA wire 21.

In the holding constant current transition control (C), the supply current to the SMA wire 21 is gradually reduced to the holding constant current value. Once becoming the holding constant current value, the current value of the supply current is maintained at the holding constant current value.

Thereafter, when the resistance value of the SMA wire 21 reaches the target resistance value 3, the control shifts the main control status to the near-point focus holding control SC2. In the near-point focus holding control SC2, control is performed so that the moving member 30 is substantially located at a position accounting for the amount of movement of the moving member 30 due to the radius-of-curvature difference at the time of bending. This is for allowing the lens 24 to be swiftly moved to the far-point focus position upon an instruction to switch from the near-point focus to the far-point focus.

In the near-point focus holding control SC2, first the control performs the reheating control (D-1). In the reheating control (D-1), the SMA wire 21 of the SMA wire 21 is further heated and contracted through the constant current control with the second constant current value. When the resistance value of the SMA wire 21 becomes the target resistance value 2, the control moves from the reheating control (D-1) to the holding current changing control (D-2).

In the holding current changing control (D-2), the supply current to the SMA wire 21 is reduced to the current value larger by the first predetermined value than the previous holding current value.

Further, if it takes the predetermined time or more for the resistance value of the SMA wire 21 to reach the target resistance value 3, the holding current value is reduced to the second predetermined value.

Thus, in the near-point focus holding control SC2, the SMA wire 21 is reheated if the resistance value of the SMA wire 21 increases to the target resistance value 3. Each time the SMA wire 21 is reheated, the current value of the holding current is increased by the first predetermined value. This allows control such that the resistance value of the SMA wire 21 is stabilized as quickly as possible with consideration for a low ambient temperature in the distal end portion 12 of the insertion section 7.

If the resistance value of the SMA wire 21 does not reach the target resistance value 3 after the lapse of the predetermined time or more, the current value of the holding current is reduced by the second predetermined value. This allows control such that the number of occurrences of the reheating is minimized when the balance of the temperature in the distal end portion 12 of the insertion section 7 is maintained. Reducing the number of occurrences of the reheating allows less decrease in the durability of the SMA wire 21.

Thus, the endoscope system in the above-described embodiment can improve the lens movement responsiveness, the power saving in the lens driving control, and the durability of the shape memory element.

The present invention is not limited to the above-described embodiment but allows various modifications and alterations without departing from the spirit of the present invention.

What is claimed is:

1. An endoscope system including an image pickup device picking up an image of an object and an objective optical system, the endoscope system comprising:

an actuator having a shape memory element and driving a moving member for moving the objective optical system;

an actuator drive unit driving the actuator;

a resistance value detection section detecting a resistance value of the shape memory element for detecting a position of the moving member;

an instruction input unit to which an instruction to move the objective optical system is inputted; and a control section outputting a driving signal to the actuator drive unit on a basis of the instruction inputted to the instruction input unit and the position of the moving member corresponding to the resistance value detected by the resistance value detection section, wherein in response to a moving instruction inputted to the instruction input unit to move the objective optical system from a first position to a second position, the control section outputs the driving signal so that a current for moving the moving member from the first position to a third position beyond the second position is passed through the shape memory element, when the moving member reaches the third position, the control section outputs the driving signal so that a first constant current is passed through the shape memory element until the resistance value of the shape memory element becomes a first resistance value smaller than a resistance value of the shape memory element corresponding to the third position and larger than a minimum resistance value within a moving range of the moving member, when the resistance value of the shape memory element becomes the first resistance value, the control section outputs the driving signal so that a first holding constant current smaller than the first constant current is passed through the shape memory element, and when the resistance value of the shape memory element becomes a second resistance value larger than the first resistance value during passage of the first holding constant current through the shape memory element, the control section outputs the driving signal so that a current is passed through the shape memory element, the current being for holding the moving member at a position farther than the second position from the first position within a range in which the resistance value of the shape memory element does not reach the minimum resistance value.

2. The endoscope system according to claim 1, wherein the control section holds the moving member at the position farther than the second position from the first position by repeating: passing a second constant current through the shape memory element until the resistance value of the shape memory element becomes the first resistance value; and, when the resistance value of the shape memory element becomes the first resistance value, reducing the current passed through the shape memory element to a third current value smaller than a current value of the second constant current and passing a second holding constant current.

3. The endoscope system according to claim 2, wherein the current value of the second constant current is smaller than a current value of the first constant current.

4. The endoscope system according to claim 2, wherein in holding the moving member at the position farther than the second position from the first position, the control section increases a current value of the second holding constant current by a first predetermined value when the resistance value of the shape memory element becomes the first resistance value.

5. The endoscope system according to claim 1, wherein in holding the moving member at the position farther than the second position from the first position, the control section reduces a current value of the second holding constant current by a second predetermined value when not less than a predetermined length of time is required for the resistance value of the shape memory element to become the second resistance value after start of passage of the second holding constant current through the shape memory element.

6. The endoscope system according to claim 1, comprising a nonvolatile memory storing the minimum resistance value of the shape memory element.

7. The endoscope system according to claim 1, wherein for control of passing the current through the shape memory element for moving the moving member from the first position to the third position, the control section uses proportional-plus-derivative control based on the resistance value detected by the resistance detection section and the resistance value of the shape memory element corresponding to the third position.

8. A method for controlling an endoscope actuator, the actuator having a shape memory element and driving a moving member for moving an objective optical system for an image pickup device picking up an image of an object, the actuator being controlled with: an actuator drive unit driving the actuator; a resistance value detection section detecting a resistance value of the shape memory element for detecting a position of the moving member; an instruction input unit to which an instruction to move the objective optical system is inputted; and a control section outputting a driving signal to the actuator drive unit on a basis of the instruction inputted to the instruction input unit and the position of the moving member corresponding to the resistance value detected by the resistance value detection section, the method comprising:

in response to a moving instruction inputted to the instruction input unit to move the objective optical system from a first position to a second position, the control section outputting the driving signal to the actuator drive unit so that a current for moving the moving member from the first position to a third position beyond the second position is passed through the shape memory element;

when the moving member reaches the third position, the control section outputting the driving signal to the actuator drive unit so that a first constant current is passed through the shape memory element until the resistance value of the shape memory element becomes a first resistance value smaller than a resistance value of the shape memory element corresponding to the third position and larger than a minimum resistance value within a moving range of the moving member;

when the resistance value of the shape memory element becomes the first resistance value, the control section outputting the driving signal to the actuator drive unit so that a first holding constant current smaller than the first constant current is passed through the shape memory element; and when the resistance value of the shape memory element becomes a second resistance value larger than the first resistance value during passage of the first holding constant current through the shape memory element, the control section outputting the driving signal to the actuator drive unit so that a current is passed through the shape memory element, the current being for holding the moving member at a position farther than the second position from the first position within a range in which the resistance value of the shape memory element does not reach the minimum resistance value.

9. The method for controlling the endoscope actuator according to claim 8, wherein
the control section holds the moving member at the position farther than the second position from the first position by repeating: passing a second constant current through the shape memory element until the resistance value of the shape memory element becomes the first resistance value; and, when the resistance value of the shape memory element becomes the first resistance value, reducing the current passed through the shape memory element to a third current value smaller than a current value of the second constant current and passing a second holding constant current.

10. The method for controlling the endoscope actuator according to claim 9, wherein
the current value of the second constant current is smaller than a current value of the first constant current.

11. The method for controlling the endoscope actuator according to claim 9, wherein
in holding the moving member at the position farther than the second position from the first position, the control section increases a current value of the second holding constant current by a first predetermined value when the resistance value of the shape memory element becomes the first resistance value.

12. The method for controlling the endoscope actuator according to claim 8, wherein in holding the moving member at the position farther than the second position from the first position, the control section reduces a current value of the second holding constant current by a second predetermined value when not less than a predetermined length of time is required for the resistance value of the shape memory element to become the second resistance value after start of passage of the second holding constant current through the shape memory element.

13. The method for controlling the endoscope actuator according to claim 8, wherein for control of passing the current through the shape memory element for moving the moving member from the first position to the third position, the control section uses proportional-plus-derivative control based on the resistance value detected by the resistance detection section and the resistance value of the shape memory element corresponding to the third position.

\* \* \* \* \*